US008049137B2

(12) United States Patent
Holman et al.

(10) Patent No.: US 8,049,137 B2
(45) Date of Patent: Nov. 1, 2011

(54) LASER SHOCK PEENING OF MEDICAL DEVICES

(75) Inventors: Thomas Holman, Princeton, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1309 days.

(21) Appl. No.: 10/778,841

(22) Filed: Feb. 13, 2004

(65) Prior Publication Data

US 2005/0182478 A1   Aug. 18, 2005

(51) Int. Cl.
B23K 26/00 (2006.01)

(52) U.S. Cl. .......... 219/121.85; 219/121.78; 219/121.84

(58) Field of Classification Search ............ 219/121.85, 219/121.6, 121.84, 121.78, 121.73, 121.76, 219/121.77; 623/1.1–1.54, 900–901
See application file for complete search history.

(56) References Cited

U.S. PATENT DOCUMENTS

| | | | |
|---|---|---|---|
| 3,850,698 A | | 11/1974 | Mallozzi et al. |
| 4,401,477 A | | 8/1983 | Clauer et al. |
| 5,766,192 A | * | 6/1998 | Zacca ............................ 606/159 |
| 5,846,057 A | * | 12/1998 | Ferrigno et al. .......... 416/241 R |
| 5,902,254 A | | 5/1999 | Magram |
| 5,911,891 A | | 6/1999 | Dulaney et al. |
| 5,954,740 A | * | 9/1999 | Ravenscroft et al. ......... 606/194 |
| 5,987,042 A | | 11/1999 | Staver et al. |
| 6,002,706 A | | 12/1999 | Staver et al. |
| 6,021,154 A | | 2/2000 | Unternahrer |
| 6,049,058 A | | 4/2000 | Dulaney et al. |
| 6,094,260 A | * | 7/2000 | Rockstroh et al. ............ 356/35.5 |
| 6,110,192 A | * | 8/2000 | Ravenscroft et al. ......... 606/194 |
| 6,198,069 B1 | * | 3/2001 | Hackel et al. ............... 219/121.6 |
| 6,410,884 B1 | | 6/2002 | Hackel et al. |
| 6,423,935 B1 | * | 7/2002 | Hackel et al. ............ 219/121.85 |
| 6,474,135 B1 | | 11/2002 | Clauer et al. |
| 6,479,790 B1 | | 11/2002 | Graham et al. |
| 6,492,615 B1 | | 12/2002 | Flanagan |
| 6,657,160 B2 | * | 12/2003 | Hackel et al. ............ 219/121.85 |
| 6,664,506 B2 | | 12/2003 | Clauer et al. |
| 6,670,577 B2 | | 12/2003 | Staver et al. |
| 6,670,578 B2 | | 12/2003 | Hackel et al. |
| 6,904,658 B2 | * | 6/2005 | Hines ............................... 29/423 |
| 7,335,426 B2 | * | 2/2008 | Marton et al. ................. 428/544 |
| 2002/0095208 A1 | | 7/2002 | Gregorich et al. |

(Continued)

FOREIGN PATENT DOCUMENTS

| | | |
|---|---|---|
| EP | 0 924 306 A2 | 6/1999 |
| EP | 1 122 321 A2 | 8/2001 |
| EP | 1 188 842 A1 | 3/2002 |
| EP | 1803483 A1 | 7/2007 |

OTHER PUBLICATIONS

Hill et al., "Laser Peening Technology", Advanced Material & Processes, Aug. 2003, pp. 65-67.

(Continued)

Primary Examiner — M. Alexandra Elve
(74) Attorney, Agent, or Firm — Seager, Tufte & Wickhem, LLC

(57) ABSTRACT

A laser shock peening process for producing one or more compressive residual stress regions in a medical device is disclosed. A high-energy laser apparatus can be utilized to direct an intense laser beam through a confining medium and onto the target surface of a workpiece. An absorption overlay disposed on the target surface of the workpiece absorbs the laser beam, inducing a pressure shock wave that forms a compressive residual stress region deep within the workpiece. Medical devices such as stents and guidewires having one or more of these compressive residual stress regions are also disclosed.

23 Claims, 13 Drawing Sheets

U.S. PATENT DOCUMENTS

| | | | |
|---|---|---|---|
| 2003/0038123 | A1 | 2/2003 | Dykes et al. |
| 2003/0062350 | A1 | 4/2003 | Staver et al. |
| 2003/1021378 | | 11/2003 | Dykes et al. |
| 2004/0011774 | A1 | 1/2004 | Tenaglia et al. |
| 2004/0016278 | A1 | 1/2004 | Douman et al. |
| 2004/0224179 | A1* | 11/2004 | Sokol et al. .......... 428/610 |
| 2005/0049690 | A1 | 3/2005 | Boismier et al. |
| 2005/0059994 | A1* | 3/2005 | Walak et al. .......... 606/200 |
| 2005/0182478 | A1 | 8/2005 | Holman et al. |
| 2007/0100285 | A1 | 5/2007 | Griffin et al. |

OTHER PUBLICATIONS

Minamitani et al., "Excimer Laser Processing Ssytem Using Holographic Optical Elements", Mitsubishit Electric Advance, Dec. 1997, 3 pgs.

Nikitin at al., "High temperature fatigue behavior and residual stress stability of laser-shock peened and deep rolled austenitic steel AISI 304", Scripta Materialia 50 (2004) pp. 1345-1350.

Peyre et al., "Corrosion Reactivity of Laser-Peened Steel Surfaces", Journal of Materials Engineering and Performance, vol. 9(6) Dec. 2000, pp. 656-662.

VanAken, "Engineering Concepts: Laser Shock Processing", University of Missouri-Rolla, Dept. of Metallurical Engineering. http:/hvww.industrialheating.com/CDA/ArticleInfrmation/features/BNP_Features_Ite, Nov. 7, 2003, 2 pgs.

Zhang et al., "Micro Scale Laser Shock Processing of Metallic Components", Journal of Manufacturing Science and Engineering, May 2002, vol. 124, pp. 369-378.

* cited by examiner

LASER SHOCK PEENING OF MEDICAL DEVICES

FIELD OF THE INVENTION

The present invention relates to medical devices and methods of manufacturing such devices. More specifically, the present invention pertains to laser shock peening of medical devices.

BACKGROUND OF THE INVENTION

Medical devices such as stents, guidewires, catheters, intravascular filters, needles, and needle stylets are used in performing a wide variety of medical procedures within the body. To permit such devices to be inserted into relatively small regions such as the cardiovascular and/or peripheral anatomies, the various components forming the device must be made relatively small while still maintaining a particular performance characteristic within the body such as high flexibility and fatigue strength. In the design of stents, for example, it is desirable to make the struts highly flexible to permit the stent to be easily collapsed and inserted into a deployment device such as a sheath or catheter. The stent must also be resistant to the formation of cracks or other irregularities that can reduce the performance of the device. Crack propagation may occur, for example, in regions of the stent subjected to high tensile stresses such as at joints and bending regions. Repeated expansion and contraction of the device within the body may accelerate the growth of these cracks, reducing the performance of the device over time.

A number of processes have been used to impart flexibility and fatigue strength to the surface of medical devices. Such processes typically include treating the medical device by annealing, work hardening, or other suitable technique to alter the physical characteristics of the material. In a shot peening process, for example, the surface of a workpiece is physically bombarded with particles or shot to form a superficial compressive residual stress region below the surface. The formation of these compressive residual stresses within the workpiece tend to negate the tensile stresses that can cause the initiation and growth of fatigue cracks, and allows the workpiece to undergo a greater amount of bending before plastically deforming.

While conventional processes such as shot peening have been used in treating medical devices, the efficacy of such processes are typically limited by the depth, and in some cases the accuracy, at which the compressive residual stress regions can be formed within the workpiece. In general, the greater the depth at which compressive residual stresses are formed within the workpiece, the greater the resistance to cracking that will result. Since many convention processes such as shot peening are limited by the depth at which the compressive residual stress region can be formed, such processes are not always effective at preventing cracks in highly flexible regions deep within the surface of the workpiece.

SUMMARY OF THE INVENTION

The present invention pertains to laser shock peening of medical devices. An illustrative laser shock peening process in accordance with an embodiment of the present invention includes the steps of providing a workpiece having a target surface to be irradiated, applying an absorption overlay onto the target surface, and directing a laser beam onto the absorption overlay to induce a pressure shock wave within the workpiece that can be used to produce one or more compressive residual stress regions therein. A high-energy laser apparatus capable of producing one or more intense laser beams may be provided to vaporize the absorption overlay material and form an interface layer of plasma above the target surface. The rapid expansion of volume and pressure at the interface layer induces a pressure shock wave within the workpiece that is greater than the dynamic yield stress of the workpiece material, creating a compressive residual stress region within the workpiece. In certain embodiments, a confining medium such as water can be provided to increase the magnitude of the induced pressure shock wave, further increasing the depth of the compressive residual stress region within the workpiece.

To form multiple compressive residual stress regions within the workpiece, a diffraction grating, prism or other similar device may be used to direct the light beam to selective locations on the workpiece target surface. In one illustrative embodiment, a holographic optical element may be employed to produce a desired laser beam pattern on the target surface of the workpiece. The holographic optical element may include a hologram that, when subjected to a laser beam, produces a desired pattern or array of compressive residual stress regions within the workpiece. In certain embodiments, for example, two adjacently pulsed laser beams can be directed simultaneously onto two locations of the target surface, inducing multiple pressure shock waves within the workpiece. The distance between the two locations on the target surface can be selected to produce a vertical compressive residual stress region deep within the workpiece formed by the overlapping of pressure shock waves. Other factors such as the laser beam intensity, duration, number of pulses, etc. may also be controlled to produce a desired compressive residual stress distribution within the workpiece.

In another illustrative laser shock peening process, multiple compressive residual stress regions may be formed within the workpiece by applying a patterned absorption overlay to the workpiece target surface. The patterned absorption overlay may comprise a patterned layer of absorptive paint, adhesive tape, or other suitable means for selectively absorbing the laser beam at certain locations above the target surface. When subjected to an intense laser beam, the patterned absorption overlay can be configured to induce multiple pressure shock waves that form a desired compressive residual stress distribution within the workpiece.

Using one or more of the aforesaid processes, a medical device such as a stent, guidewire, intravascular filter, guide catheter, needle, needle stylet, etc. may be formed having one or more compressive residual stress regions therein. In one illustrative embodiment, for example, a stent having a number of struts may include one or more compressive residual stress regions formed therein. In use, the compressive residual stress regions increase the flexibility and fatigue strength of the material at these locations, allowing the use of thinner struts with less disruption to the bloodstream. In another illustrative embodiment, a guidewire may include a core wire with one or more compressive residual stress regions formed in a pattern along the length of the guidewire, or within the entire guidewire. In certain embodiments, the one or more compressive residual stress regions may be formed about a joint used to fuse various components of the guidewire together. In use, the compressive residual stress regions can be used to impart one or more desired characteristics to the guidewire such as increased flexibility and strength.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
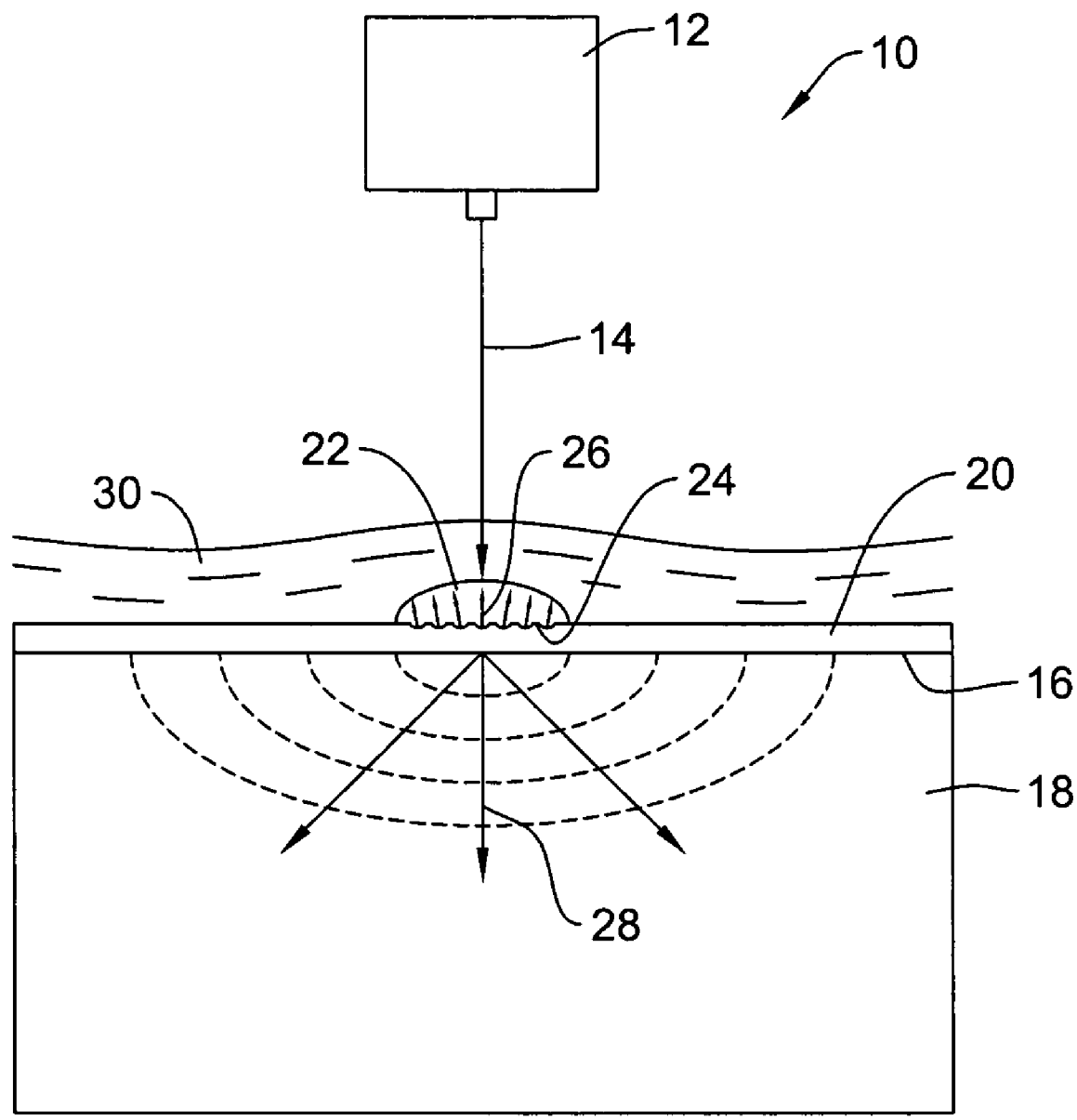
FIG. 1 is a diagrammatic view showing an illustrative laser shock peening process for use in producing a compressive residual stress region within a workpiece.

FIG. 1 is a diagrammatic view showing an illustrative laser shock peening process for use in producing a compressive residual stress region within a workpiece. The laser shock peening process, represented generally by reference number 10, includes a high-energy laser apparatus 12 configured to direct an intense laser beam 14 onto the target surface 16 of a metallic workpiece 18. The workpiece 18 may comprise one or more components of a stent, guidewire, catheter, intravascular filter, or other medical device wherein characteristics such as flexibility and fatigue strength are desirable. In certain embodiments, for example, the workpiece 18 may comprise a sheet or tube of material used in the construction of a stent, or a core wire used in the construction of an intravascular guidewire.

The inventive techniques described herein can be used to form any number of devices having a metal, metal-polymer, or metal-metal composition, or materials including a carbon ceramic material and/or ceramic coatings. Examples of suitable metals include, but are not limited to, copper, aluminum, titanium, nickel, platinum, tantalum, nickel-titanium alloy, and steel-based alloys such as stainless steel. Composites of one or more of these materials may also be used, if desired.

A sacrificial absorption overlay 20 disposed over the target surface 16 of the workpiece 18 may be employed to absorb the laser beam 14 irradiated from the high-energy laser apparatus 12. The absorption overlay 20 may comprise one or more materials that are substantially opaque to radiation. The absorption overlay 20 may include, for example, a layer or sheet of paint (e.g. iron oxide or carbon), pentaerythritol tetranitrate (PETN), bismuth, aluminum, iron, lead, cadmium, tin, zinc, graphite, or other suitable material. In certain embodiments, a biocompatible absorption overlay 20 including carbon or high-density polytetrafluoroethylene (HDPTFE) loaded with tungsten filler may be employed. Adhesive or gel materials that are opaque to radiation may also be used in certain embodiments.

In addition to absorbing radiation from the laser beam 14, the absorption overlay 20 acts as a thermal barrier to protect the workpiece 18 from thermal effects generated during the laser peening process. The ability to prevent the transfer of heat into the workpiece 18 is important to maintain the desired performance characteristics of the material. With respect to shape-memory nickel-titanium alloys, for example, the absorption overlay 20 prevents undesired thermal effects within the material that can alter the memory and/or flexibility characteristics of the material.

To induce a pressure shock wave within the workpiece 18, the high-energy laser apparatus 12 should be configured to provide an intense laser beam. In one illustrative embodiment, a high-energy laser apparatus may include a 600-Watt (100-Joule) neodymium-doped glass laser capable of producing a 20-nanosecond laser beam pulse having an energy density of about 200 J/cm$^2$. The resultant shock wave produced by the high-energy laser apparatus 12 may have a pressure of greater than 1 GPa, which is above the yield stress of most metals.

When irradiated with the intense laser beam 14, the target surface 16 of the metallic workpiece 18 instantly vaporizes, forming an expanding gas release of plasma 22 at interface 24, which is then further heated by the incident laser beam 14. As the high-temperature plasma is formed at the interface 24, its pressure is increased to a range of about 1 to 10 GPa. This increase in temperature and pressure causes the plasma 22 to expand in a direction indicated generally by the upwardly pointed arrows 26, inducing a pressure shock wave within the workpiece 18. As indicated by the downwardly directed arrows 28, the induced pressure shock wave then propagates in part into the interior of the workpiece 18 along a semi-circular wavefront.

In certain embodiments, a confining medium 30 transparent to the irradiated laser beam 14 can be used to increase the magnitude of the induced pressure shock wave, in some cases by a factor of 5 or more in comparison to an open-air condition. The confining medium 30 may comprise any number of suitable materials known in the art, including, for example, water, glass, quartz, sodium silicate, fused silica, potassium chloride, sodium chloride, polyethylene, fluoropolymers, and nitrocellulose. The confining medium 30 may be formed integral with the absorption overlay 20, or may comprise a separate layer located adjacent to the absorption overlay 20.

As the induced pressure shock wave is transmitted into the workpiece 18, the region beneath the shocked area undergoes both plastic and elastic deformations, forming compressive residual stresses deep within the workpiece 18. The formation of compressive residual stresses within the workpiece 18 can be used to impart one or more desired characteristics to the medical device such as increased flexibility and resistance to cracking. Other characteristics such as corrosion resistance and wear resistance can also be achieved using a laser shock peening process.

Figure 2:
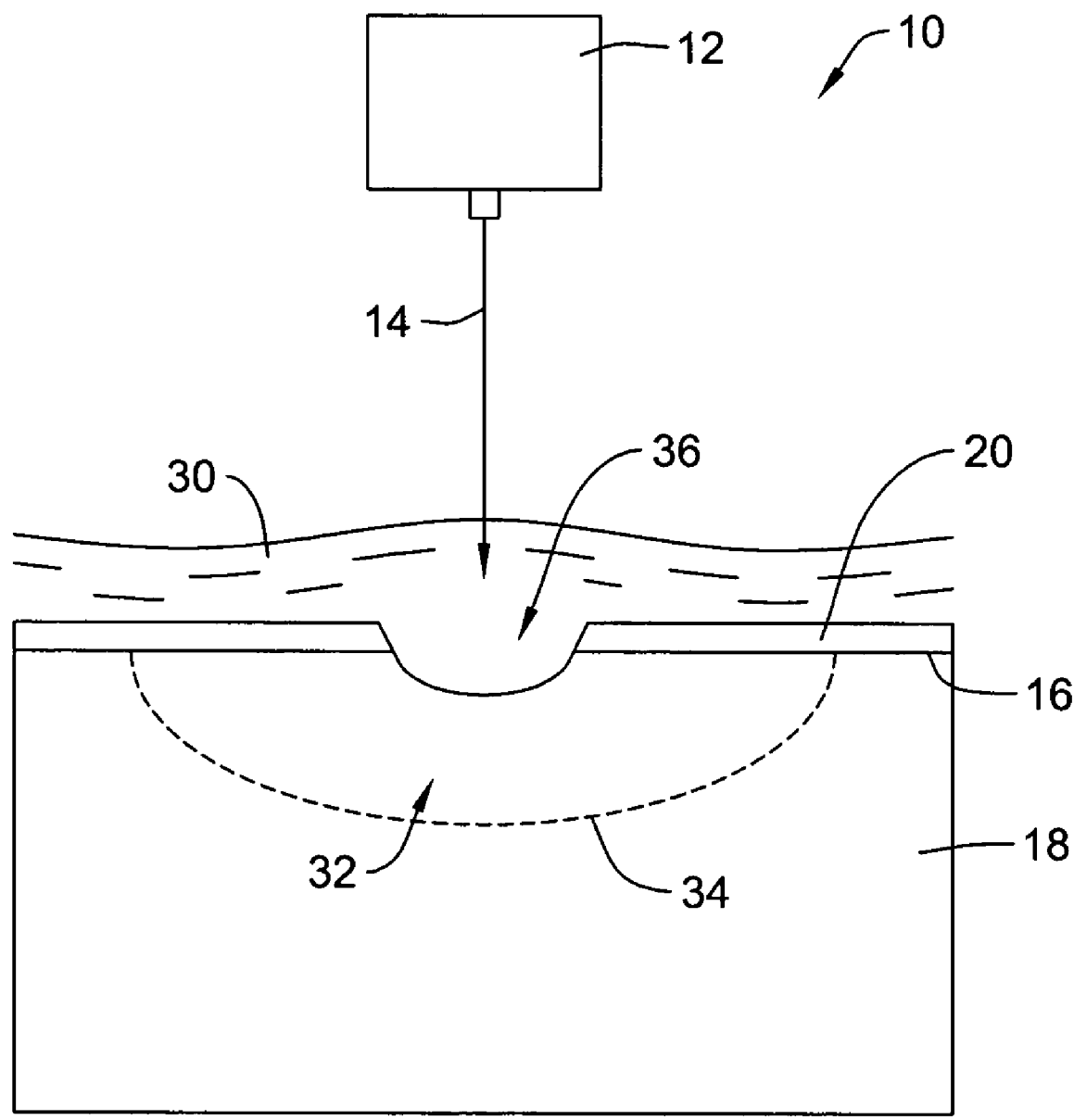
FIG. 2 is a diagrammatic view showing the formation of a single compressive residual stress region within the workpiece of FIG. 1.

FIG. 2 is a diagrammatic view showing the formation of a single compressive residual stress region 32 within the workpiece of FIG. 1. As indicated by the semi-circular dashed line 34 in FIG. 2, the compressive residual stress region 32 may extend from an indent 36 formed on the target surface 16 of the workpiece 18 to a location deep within the interior of the workpiece 18. In certain embodiments, for example, the above process can be used to form a compressive residual stress region at a depth of about 0.05 to 0.1 inches or greater into the workpiece 18.

The magnitude and depth of the compressive residual stress region 32 can be controlled by the amount of energy delivered to the irradiated area, and the dwell time of the laser beam 14. The amount of energy delivered to the irradiated area is governed by the power at which the beam is generated, by any attenuation of the laser beam, by the degree of beam focusing, and by the spatial characteristics of the laser beam. By increasing the intensity of the laser beam 14, for example, the magnitude of the induced pressure shock wave can be increased to provide greater compressive residual stresses within the workpiece 18. Other characteristics such as the acoustic impedance of the workpiece 18 material(s) may also have an effect on the magnitude and depth at which compressive residual stresses are formed in the workpiece 18.

The laser apparatus 12 can be configured to emit either a continuous or pulsed laser beam 14 onto the target surface 16 of the workpiece 18. In a pulsed laser beam configuration, the dwell time can be controlled by varying the pulse duration and frequency of the emitted beam. A similar result can be obtained with a continuous laser beam configuration through the use of a mechanical or optical shutter. All other factors being the same, an increase in dwell time results in the formation of compressive residual stress regions of greater magnitude and depth. Thus, by altering the pulse duration and/or frequency of the laser beam, a desired compressive residual stress distribution can be achieved within the workpiece 18.

Figure 3:
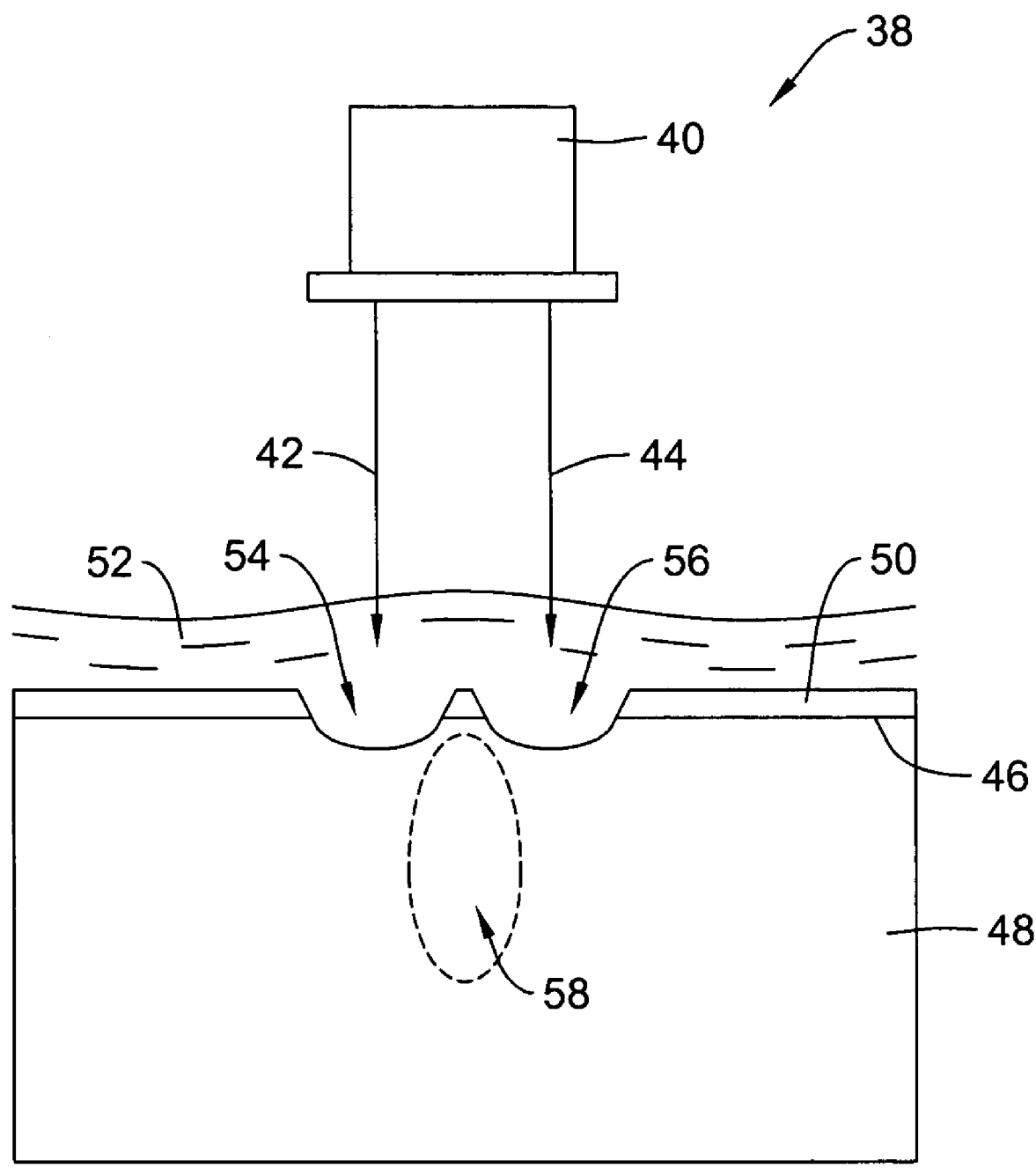
FIG. 3 is a diagrammatic view showing the formation of a vertical compressive residual stress region within a workpiece using another illustrative laser shock peening process.

FIG. 3 is a diagrammatic view showing the formation of a vertical compressive residual stress region within a workpiece using another illustrative laser shock peening process. The laser shock peening process, represented generally by reference number 38, includes the use of a high-energy laser apparatus 40 that directs two intensive laser beams 42,44 onto the target surface 46 of a workpiece 48. As with other embodiments described herein, the workpiece 48 may comprise one or more components of a stent, guidewire, catheter, intravascular filter, or other medical device. A sacrificial absorption overlay 50 disposed over the target surface 46 of the workpiece 48 may be utilized to absorb the two irradiated laser beams 42,44. A confining medium 52 of water or other suitable transparent material may also be used to increase the magnitude of the induced pressure shock wave.

The high-energy laser apparatus 40 can be configured to simultaneously pulse the two laser beams 42,44 through the confining medium 52 and onto the absorption overlay 50. The intensity of each laser beam 42,44 can be made sufficient to induce two separate pressure shock waves within the workpiece 48, each emanating from a location immediately below the respective laser beam 42,44. As the pressure shock wave travels through the workpiece 48, first and second indents 54,56 are formed on the target surface 46 of the workpiece 48.

As is further indicated by dashed lines in FIG. 3, a vertical compressive residual stress region 58 located immediately below the midpoint of the first and second indents 54,56 can be formed within the workpiece 48. At this region 58, the two pressure shock waves induced by the two laser beams 42,44 overlap and collide to form a highly concentrated compressive residual stress region 58 within the workpiece 48. The shape and depth of the region 58 is dependent in part on the spacing between the two laser beams 42,44, and the magnitude of the induced pressure shock waves. As is discussed in greater detail below with respect to several illustrative medical devices, one or more of these vertical compressive residual stress regions 58 can be used to impart characteristics such as increased flexibility and fatigue strength to selective portions of the medical device, in some cases allowing smaller components to be used.

The laser beams 42,44 may be produced using multiple laser sources, or through the use of a single laser source in conjunction with a diffraction grating, prism, or other similar device. In certain embodiments, for example, the high-energy laser apparatus may include a type of diffraction grating called holographic optical element (HOE), which can be used to spatially modulate a single laser beam to produce a desired pattern onto the surface of the workpiece.

Figure 4:
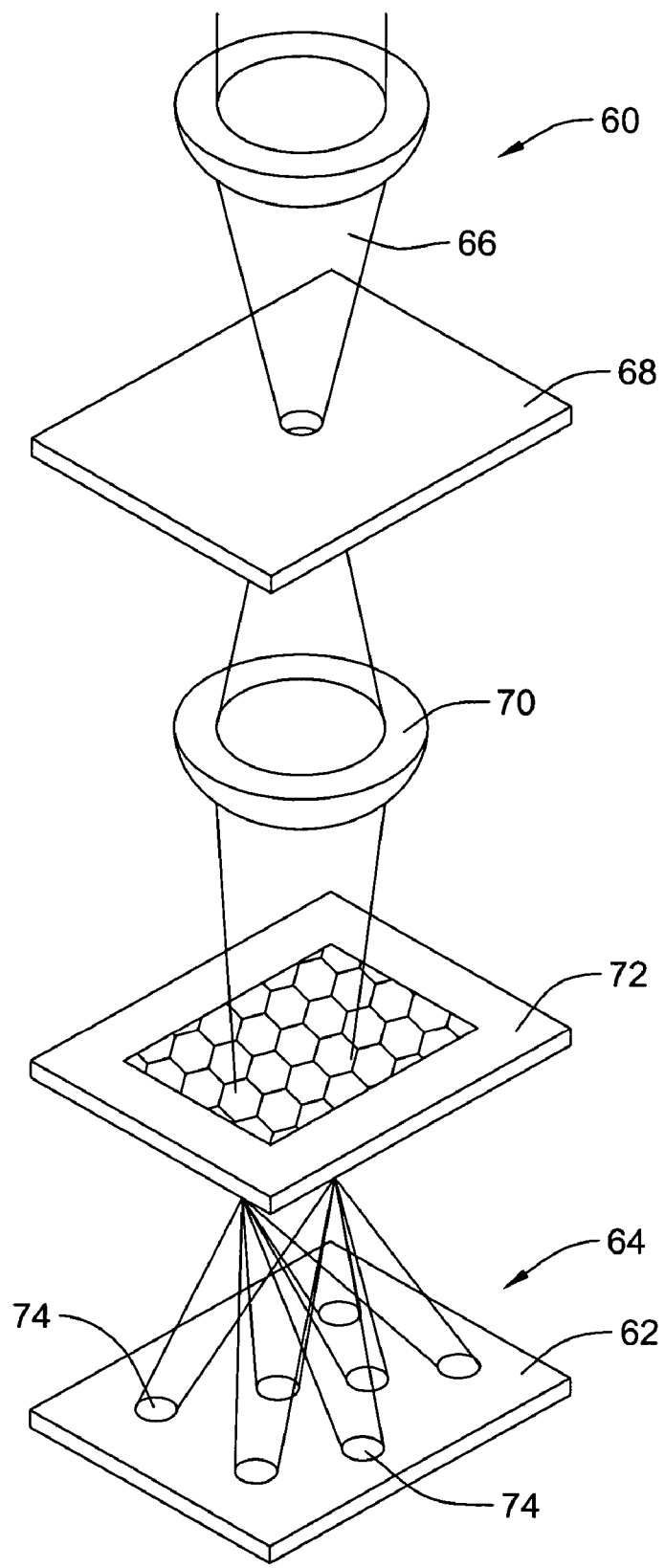
FIG. 4 is a diagrammatic view of a holographic optical element configured to produce a pattern or array of compressive residual stress regions within a workpiece.

FIG. 4 is a diagrammatic view an illustrative holographic optical element 60 that can be used to produce a desired laser beam pattern onto the target surface 62 of a workpiece 64. As shown in FIG. 4, the holographic optical element 60 may include a laser beam 66, a simple aperture mask 68, a transfer lens 70, and a hologram 72. As the laser beam 66 is received from the transfer lens 70, it is spatially modulated by the hologram 72, directing multiple spatial frequency components of the laser beam onto the target surface 62 of the workpiece 64. The spatial distribution of these components can be adapted to provide a desired pattern or array on the target surface 62. In the illustrative embodiment of FIG. 4, for example, the holographic optical element 60 is configured to produce a complex pattern of indents 74 at various locations on the target surface 62. The indents 74 may include a pattern of dots, lines, or other desired geometrical shape. In use, these indents 74 form compressive residual stresses deep within the workpiece 64 that can be used to impart greater flexibility and fatigue strength to the medical device.

Figure 5:
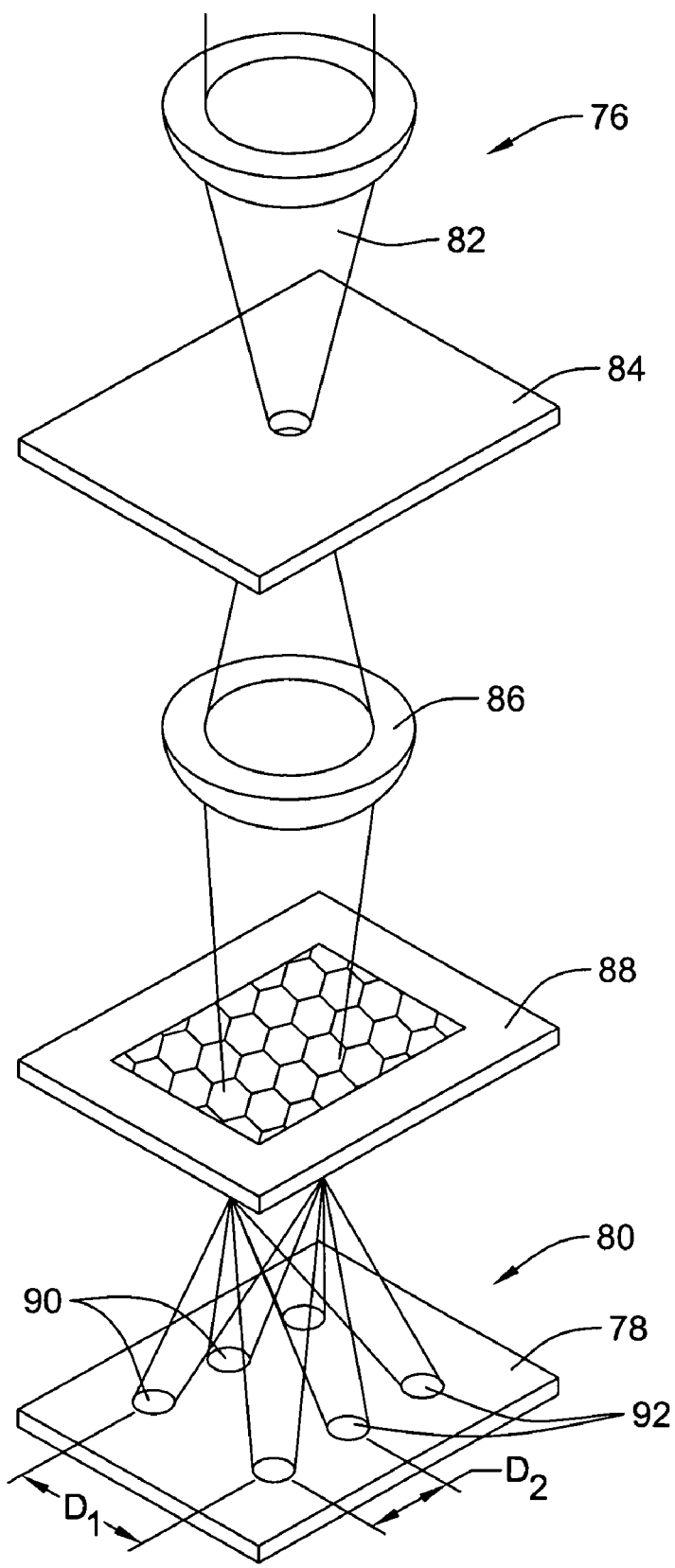
FIG. 5 is a diagrammatic view of another holographic optical element configured to produce a linear array of compressive residual stress regions within a workpiece.

FIG. 5 is a diagrammatic view of another illustrative holographic optical element 76 configured to produce a longitudinal pattern or array of compressive residual stress regions onto the target surface 78 of a workpiece 80. As with the embodiment of FIG. 4, the holographic optical element system 76 may include a laser beam 82, a simple aperture mask 84, a transfer lens 86, and a hologram 88. In the illustrated embodiment of FIG. 5, however, the hologram 88 can be configured to produce two lines of indents 90,92 on the target surface 78. Each line may be spaced apart by a distance $D_1$ on the target surface 78, with each adjacent indent 90,92 on a particular line being spaced apart a distance $D_2$ with respect to each other.

In certain embodiments, the distance $D_1$ between each line of indents 90,92 can be selected to produce multiple vertical compressive residual stress regions within the workpiece 80. In the embodiment depicted in FIG. 5, for example, multiple vertical compressive residual stress regions may be formed within the workpiece 80 along a line substantially parallel and midway between the two lines of indents 90,92. The vertical compressive residual stress regions may be formed, for example, by spacing the indents 90,92 an appropriate distance $D_1$ apart sufficient to cause the induced pressure shock waves to overlap and collide. The distance $D_2$ between each adjacent indent 90,92 on a line may also be selected to cause overlap of the pressure shock waves, further increasing the amount of compressive residual stress imparted to the workpiece 80. Thus, by selecting distances $D_1$ and $D_2$ to produce multiple overlapping pressure shock waves, a desired compressive residual stress distribution can be formed within the workpiece 80.

The formation of multiple pressure shock waves within the workpiece can also be accomplished through the use of a patterned absorption overlay that is adapted to selectively absorb the laser pulse at only certain locations above the workpiece target surface. In certain embodiments, for example, a patterned absorption overlay of black paint can be applied to the workpiece. Using laser micro-texturing techniques known in the art, a pattern of absorptive dots, lines or other desired geometric pattern can be created on the absorption overlay. An inkjet patterning technique can also be employed in certain embodiments, if desired. When subjected to a large area laser beam, the patterned absorption overlay can be configured to produce multiple pressure shock waves within the workpiece at the absorptive regions of the overlay. As with other embodiments herein, the intensity, duration, and arrangement of the absorptive pattern can be selected to produce a desired compressive residual stress distribution within the workpiece.

Figure 6:
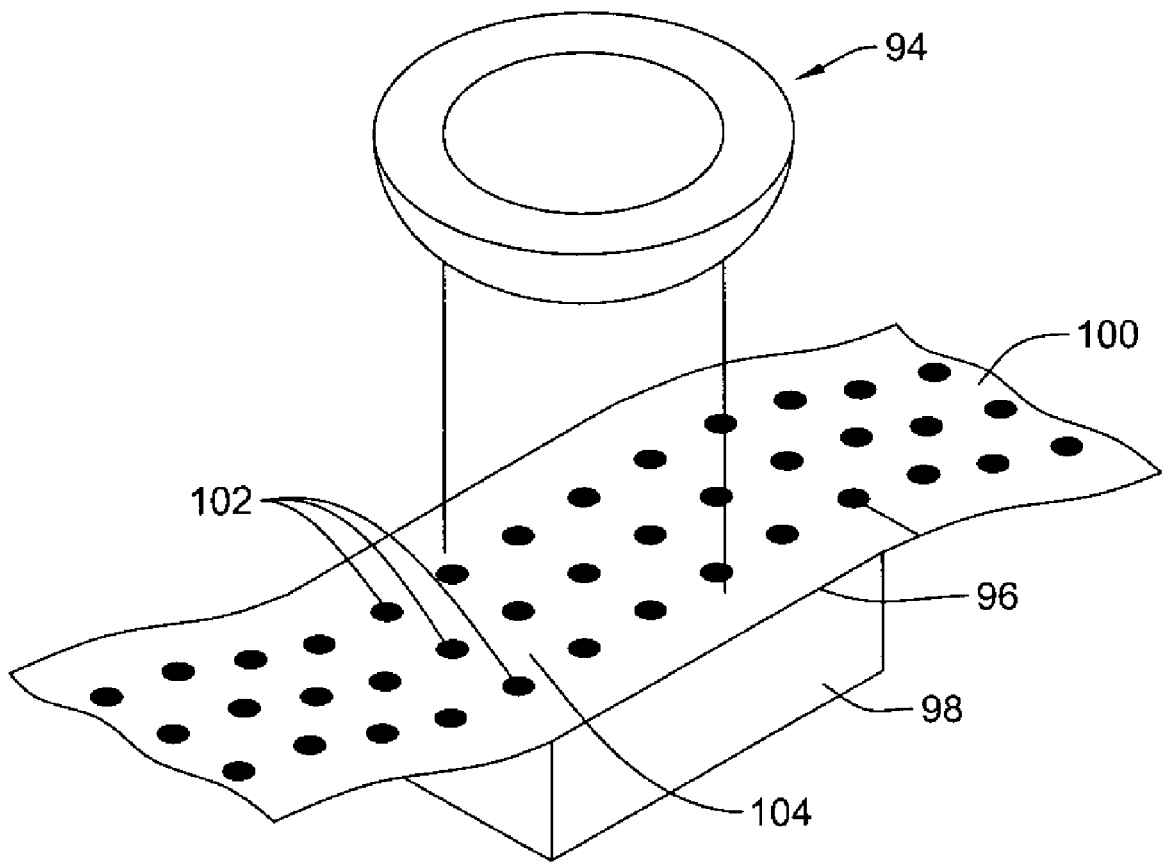
FIG. 6 is a diagrammatic view showing a patterned absorption overlay that can be used to form multiple compressive residual stress regions within a workpiece.

In one such embodiment depicted in FIG. 6, a high-energy laser apparatus 94 employing a single laser source can be configured to produce multiple pressure shock waves within the target surface 96 of a workpiece 98 using a strip of patterned adhesive tape 100 for the absorption overlay. The patterned adhesive tape 100 may include an adhesive backing that allows the adhesive tape 100 to be applied directly to the surface 96 of the workpiece 98 with no gaps.

As further shown in FIG. 6, the patterned adhesive tape 100 may include a number of absorptive dots 102 configured to absorb a portion of the laser beam irradiated from the high-energy laser apparatus 94. The absorptive dots 102 can be spaced apart from each other by a transparent region 104 of the patterned adhesive tape 100, which unlike the absorptive dots 102, does not absorb the radiation emitted from the laser apparatus 94. In use, the high-energy laser apparatus 94 can be configured to emit a large area laser beam through a transparent confining medium (not shown) and onto the patterned adhesive tape 100. As the laser beam is irradiated onto the patterned adhesive tape 100, the absorptive dots 102 absorb the laser beam, inducing a number of pressure shock waves that can be used to form a desired compressive residual stress distribution within the workpiece 98.

Figure 7:
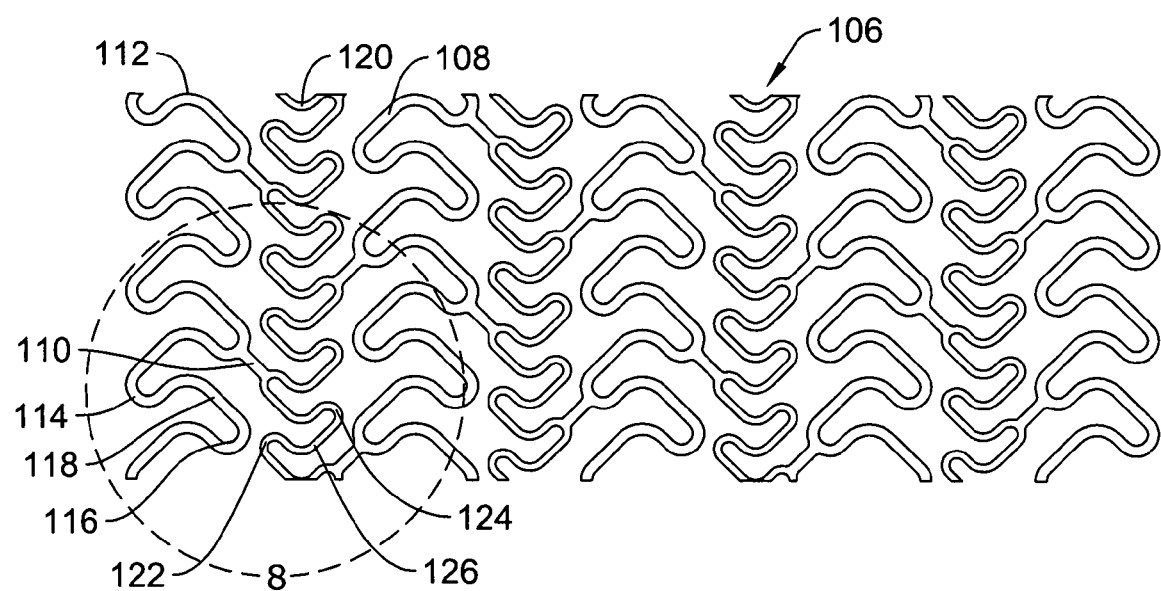
FIG. 7 is a flat layout view of an illustrative tubular stent having a number of compressive residual stress regions formed therein.

FIG. 7 is a flat layout view of an illustrative stent 106 having a number of compressive residual stress regions formed therein. The stent 106 may include a number of circumferential struts 108 that are connected to each other at various joints 110. The circumferential struts 108 may include first circumferential bands 112 having a first number of alternating first peaks 114 and first troughs 116 joined by bent struts 118. The first circumferential bands 112 may be joined at the joints 110 to second circumferential bands 120 having a second number of alternating second peaks 122 and second troughs 124 joined by bent struts 126. Together, the first and second circumferential bands 112,120 define a pathway around the periphery of the stent 106, forming a tubular structure that can be expanded within a body lumen.

To impart greater flexibility and fatigue strength, a number of compressive residual stress regions may be formed at selective locations of the stent 106 normally subjected to relatively high tensile stresses. As shown in greater detail in FIG. 8, for example, a number of indents 128 may be created by laser shock peening one or more selective peaks 114,122 and/or troughs 116,124 of the first and second circumferential bands 112,120, forming multiple compressive residual stress regions within the thickness of the stent 106 at these locations. In similar fashion, a number of indents 130 may be formed on one or more of the joints 110, forming multiple compressive residual stress regions within the thickness of the stent 106 at the joints 110. In use, these compressive residual stress regions can be used to prevent the growth or acceleration of cracks, nicks, pits, or other irregularities that can reduce the fatigue life of the stent 106. Moreover, the compressive residual stress regions can be used to increase the flexibility of the stent 106, in some cases allowing the use of thinner struts with less disruption to the bloodstream. In certain embodiments, the formation of compressive residual stress regions on the stent 106 can be used to provide texture to the stent surfaces as a final step after, for example, electropolishing, thereby reducing the contact area and friction of the stent 106 within the delivery device.

Figure 8:
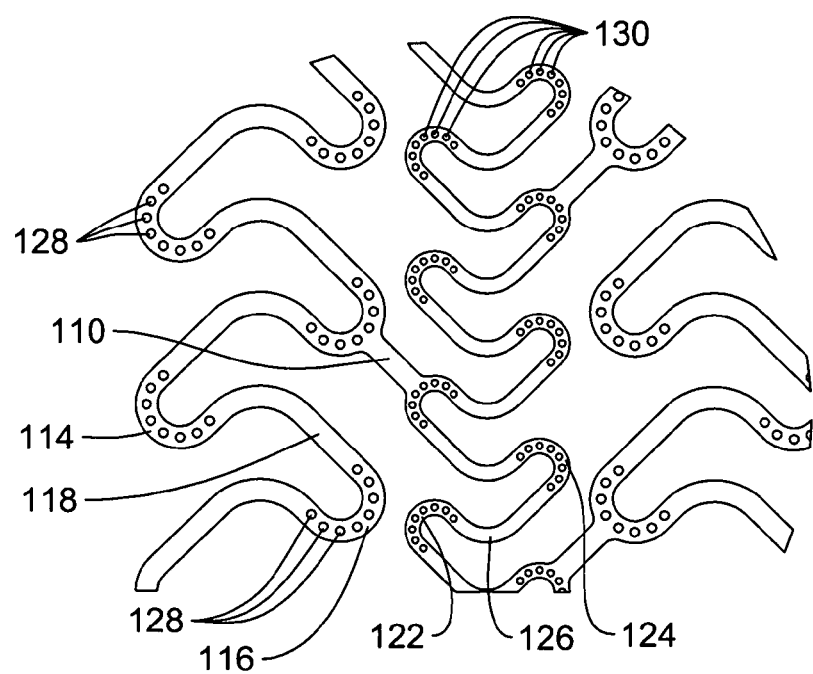
FIG. 8 is an enlarged view of a portion of the stent shown in FIG. 7.

As can be further seen in FIG. 8, each of the indents 128,130 may be closely spaced apart from each other along the length of each band 112,120. With respect to the indents 128 formed on the peaks 114,122 and/or troughs 116,124 of each band 112,120, for example, the indents 128 can be spaced apart from each other along a line located centrally on the thickness of the bands 112,120, forming compressive residual stress regions deep within the surface of the bands 112,120. The indents 128,130 can be arranged in any pattern or array to produce a desired compressive residual stress distribution within the stent 106. In certain embodiments, for example, a laser shock peening process utilizing two or more simultaneous laser beams may be utilized to form multiple vertical compressive residual stress regions within the stent 106. As with other embodiments described herein, the depth and magnitude of the vertical compressive regions may be controlled by varying the number, intensity, and duration of the laser beam pulses.

When a biocompatible absorption overlay is utilized (e.g. carbon or HDPTFE), the process of laser shock peening the stent 106 can be accomplished after the stent 106 has been crimped on the delivery system (e.g. a balloon catheter). The remaining portion of the absorption overlay not used during the laser shock peening process can then be implanted within the body while still being attached to the stent 106. By selectively peening one or more regions of the stent 106 in this manner, the inherent stresses caused by the compression of the stent 106 on the delivery device can be either reset, or altered in some other desired manner. In certain embodiments, higher securement forces can also be imparted to the crimped stent 106 by laser shock peening the stent 106 after it has been placed on the delivery device.

Figure 9:
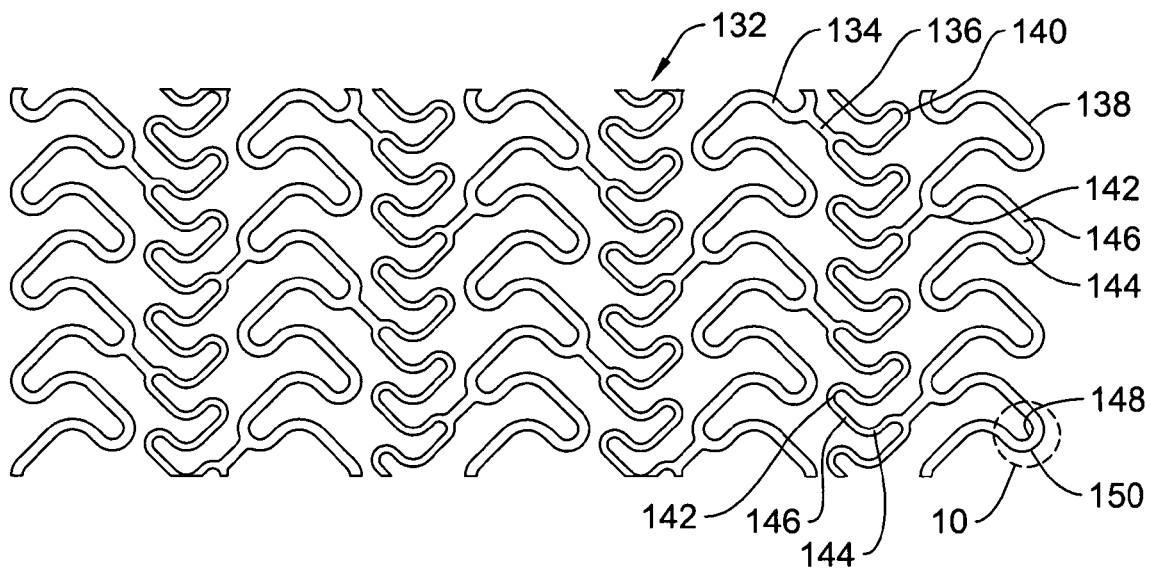
FIG. 9 is a flat layout view of another illustrative tubular stent having a number of compressive residual stress regions formed therein.

FIG. 9 is a flat layout view of another illustrative stent 132 having a number of compressive residual stress regions formed therein. Stent 132 may be configured similar to stent 106 described above, including a number of circumferential struts 134 that are connected to each other at various joints 136. The circumferential struts 134 may include a number of alternating first circumferential bands 138 and second circumferential bands 140, each including a number of alternating peaks 142 and troughs 144 joined by bent struts 146. The peaks 142 and troughs 144 may each include a U-shaped bend or other similar shape. In use, the shape of the peaks 142 and troughs 144 facilitates expansion of the stent 132 from a relatively small profile when disposed on a delivery device (e.g. a stent delivery catheter) to a larger profile during implantation within the body. In certain embodiments, for example, the struts 134 can be configured to radially expand via a balloon catheter that can be inflated to expand the stent 132 within a blood vessel. In an alternative embodiment, the stent 132 can be configured to self-expand when placed within a blood vessel, if desired.

During expansion of the stent 132 within the body, the amount of stress within the first and second circumferential bands 138,140 may increase significantly. In those embodiments in which the stent 132 is configured to expand using a balloon catheter, for example, the interior portion 148 of each peak 142 and trough 144 may undergo a significant increase in tensile stress in comparison to the outer portion 150 resulting from the decrease in the radius of curvature at this region. As a result, small cracks or other irregularities can form, reducing the performance characteristics desired in the device. Repeated expansion and contraction of the device caused by the pumping action of the heart can accelerate the growth of the cracks, reducing the performance of the stent 132 over time.

Figure 10:
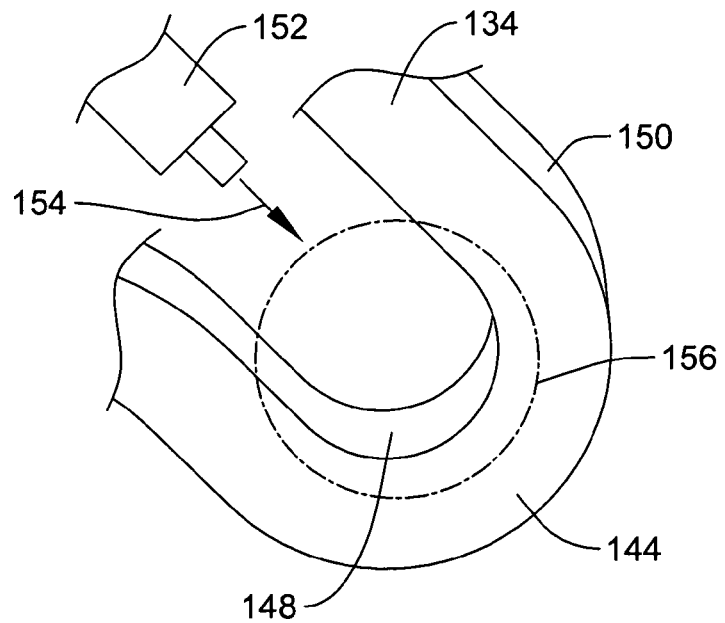
FIG. 10 is an enlarged perspective of a portion of the stent shown in FIG. 9.

To impart greater flexibility and fatigue strength at these regions, the interior portion 148 of the peaks 142 and/or troughs 144 can be laser shock peened to form one or more compressive residual stress regions therein. As can be seen in FIG. 10, for example, a high-energy laser apparatus 152 similar to laser apparatus 12 discussed above can be configured to direct an intense laser beam 154 onto the interior portion 148, inducing a shock wave within the width of the strut 134 that forms a compressive residual stress therein. The area at which the laser beam 154 is focused onto the strut 134 can be altered to either increase or decrease the size of the treatment area, as desired. In the illustrative embodiment depicted in FIG. 10, for example, the laser beam 154 is configured to treat a relatively large area of the strut 134 all at once, as is indicated generally by the region delineated by the dash lines 156. It should be understood, however, that the amount of laser focusing as well as other characteristics of the laser apparatus 152 could be controlled to produce other desired flexibility characteristics within the stent 132. Moreover, while FIG. 10 illustrates the treatment of only one of the troughs 144, it should be understood that other peaks 142 and/or troughs 144 could be similarly treated as discussed herein. In one illustrative method, for example, the laser apparatus 152 can be configured to treat one section of the stent 132, and then index to another region of the stent 132 (e.g. an adjacent peak 142 or trough 144) to treat a subsequent section, and so forth.

While the embodiments of FIGS. 7-10 illustrate the treatment of selective locations of the stent, the present invention is not limited as such. In certain embodiments, for example, it may be desirable to laser shock peen the whole stent to induce compressive residual stresses within the entire structure. In one illustrative method, a high-energy laser apparatus having a large area laser beam can be utilized to treat the entire stent structure at once. A focusing/defocusing lens or other such device can be employed to adjust the area of the incident laser beam to accommodate stents of varying size and construction, if desired.

Figure 11:
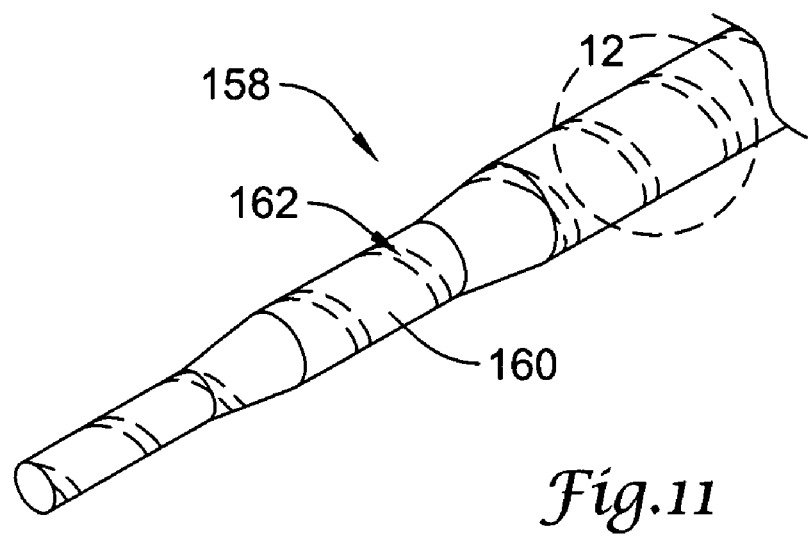
FIG. 11 is a perspective view of an illustrative guidewire having a number of compressive residual stress regions formed therein.

FIG. 11 is a perspective view of a guidewire 158 having a number of compressive residual stress regions formed therein. Guidewire 158 may include a tapered core wire 160 having a spiraled band 162 of compressive residual stress regions formed therein by a laser shock peening process. The spiraled band 162 may wrap around the outer periphery of the tapered core wire 160 along all or a portion of its length.

Figure 12:
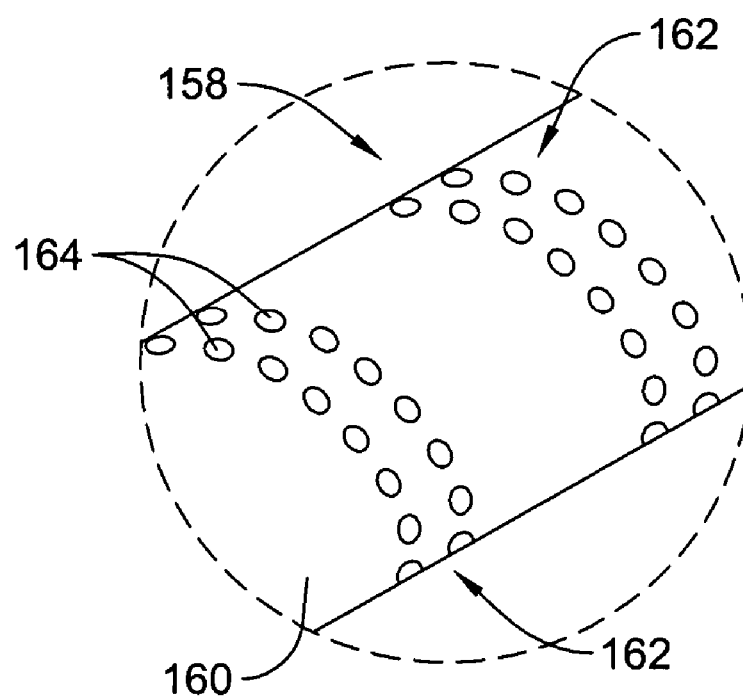
FIG. 12 is an enlarged view of a portion of the guidewire shown in FIG. 11.

As shown in greater detail in FIG. 12, the spiraled band 162 may include a number of indents 164 formed at an angle with respect to the longitudinal axis of the guidewire 158. The indents 164 can be formed, for example, by simultaneously emitting two adjacent laser beams onto the surface of the core wire 160, and then rotating and advancing the core wire 160 relative to the two laser beams. In an alternative embodiment, the core wire 160 can be held stationary and the laser apparatus rotated and advanced along the length of the core wire 160 to produce the desired pattern. A combination of these techniques may also be used to produce the desired spiral band 162 structure of FIG. 11. In one such embodiment, for example, the core wire 160 can be rotated while the high-energy laser apparatus is advanced along the length of the core wire 160.

In use, the indents 164 create a compressed plane of residual stresses at an angle to the guidewire 158 that can be used to impart greater flexibility and torqueability to the guidewire 158. While two adjacently disposed lines of indents 164 are specifically illustrated in FIG. 12, it should be understood that other alternative methods could be utilized to form compressive residual stresses within the guidewire 158. In one alternative embodiment, for example, two simultaneous laser beams can be configured to strike the surface of the core wire 160 at opposite sides (i.e. 180° alpha) apart from each other. The two laser beams can be configured to produce two separate pressure shock waves within the guidewire that collide to form a compressive residual region within the middle of the guidewire 158. In another alternative embodiment, the laser apparatus can be configured to peen the whole guidewire 158, forming compressive residual stresses within the entire structure, if desired.

Figure 13:
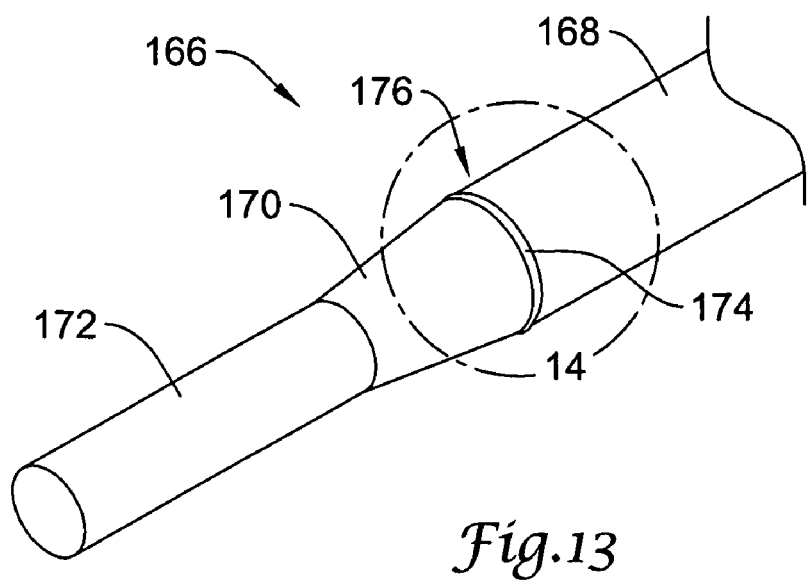
FIG. 13 is a perspective view of another illustrative guidewire having a compressive residual stress region formed about a joint.

FIG. 13 is a perspective view of another illustrative guidewire 166 having a compressive residual stress region formed about a joint. Guidewire 166 may include a proximal section 168, a tapered section 170 located distally of the proximal section 168, and a distal section 172 located further distally of the tapered section 170. Guidewire 166 may have a composite structure formed by one or more different materials that can be selected to improve characteristics such as torquability, pushability and flexibility. In one illustrative embodiment, for example, the proximal section 168 of the guidewire 166 may comprise a material different than that of the tapered section 170 and distal section 172, forming a composite guidewire that changes in flexibility along its length. In certain embodiments, for example, the proximal section 168 may comprise a relatively stiff material such as stainless steel, whereas the tapered and distal sections 170, 172 may comprise a relatively flexible material such as Nitinol.

Figure 14:
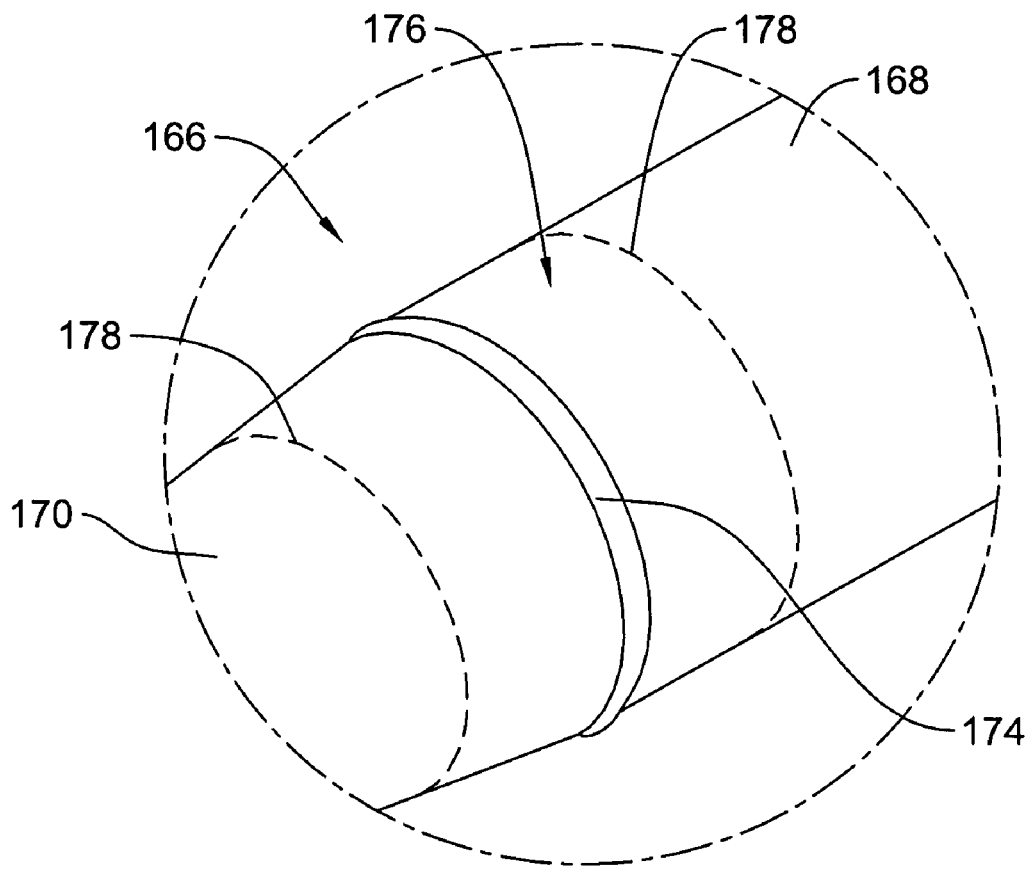
FIG. 14 is an enlarged view showing the joint of FIG. 13.

As can be further seen in FIG. 13, a weld joint 174 or other similar bonding means may be utilized about the outer periphery of the guidewire 166 to fuse the proximal section 168 to the tapered section 170. Depending on the particular welding technique employed, cracks or other irregularities may be introduced at the location of the weld joint 174, reducing the performance characteristics of the device. To prevent crack propagation, a compressive residual stress region 176 may be formed about the joint 174 by laser shock peening the outer periphery of the guidewire 166. As indicated by dashed lines 178 in FIG. 14, the compressive residual stress region 176 may comprise a circumferential band that extends about the guidewire 166 at the region of the joint 174. In use, the formation of the compressive residual stress region 176 at this region increases the flexibility and strength of the joint 174.

Figure 15:
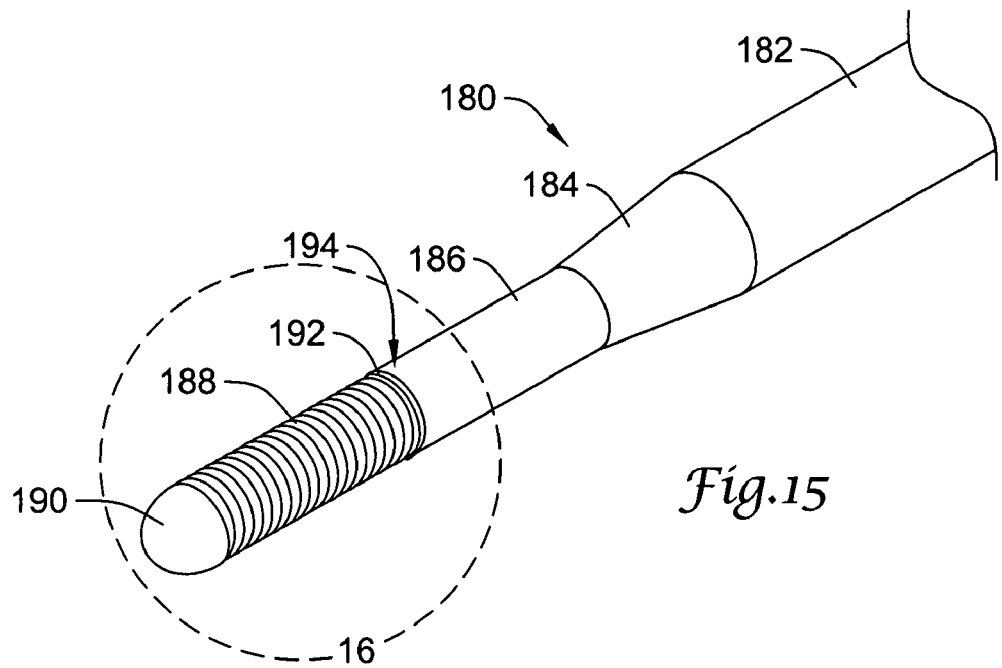
FIG. 15 is a perspective view of another illustrative guidewire having a compress residual stress region formed about a joint.

FIG. 15 is a perspective view of another illustrative guidewire 180 having a compressive residual stress region formed about a joint. Guidewire 180 is similar in construction to guidewire 166, having a proximal section 182, a tapered section 184 located distally of the proximal section 182, and a distal section 186 located further distally of the tapered section 184. In the illustrative embodiment of FIG. 15, guidewire 180 further includes a spring coil 188 and atraumatic distal tip 190, which can be used to facilitate insertion of the guidewire 180 through the tortuous anatomy.

Figure 16:
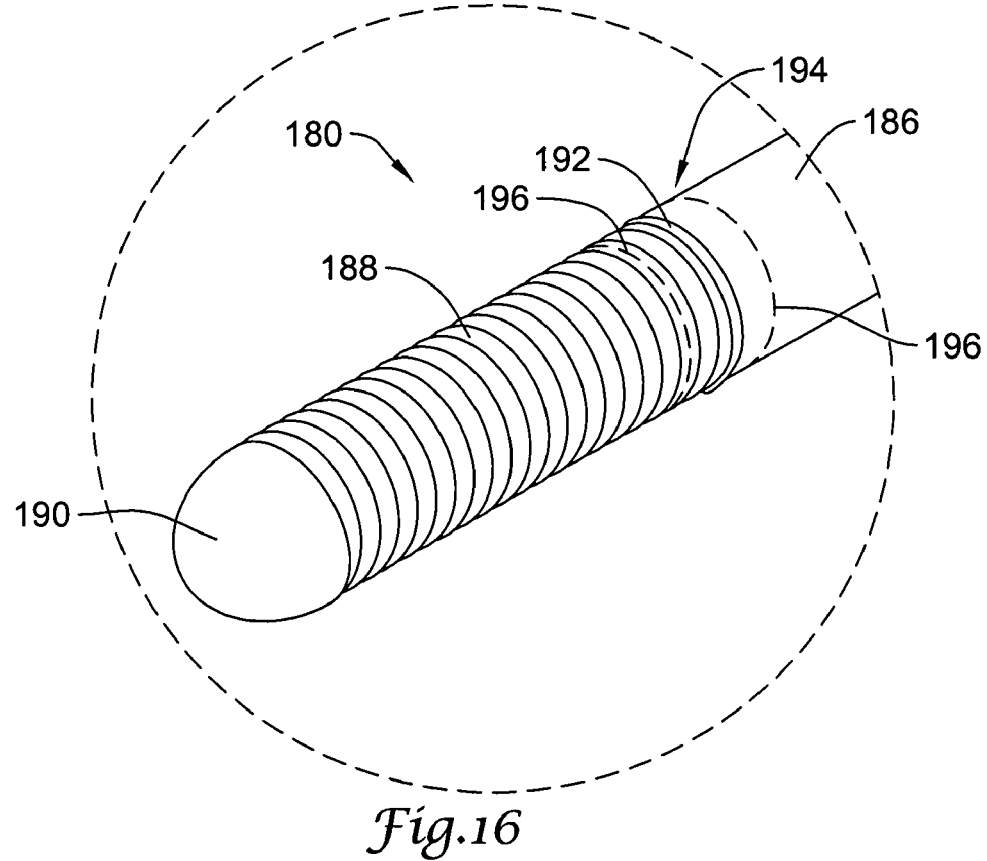
FIG. 16 is an enlarged view showing the joint of FIG. 15.

Attachment of the spring coil 188 to the distal section 186 of the guidewire 180 can be accomplished using a weld joint 192 or other suitable bonding means. To further strengthen the joint 192 and permit greater flexion of the guidewire 180, a compressive residual stress region 194 may be formed at or near the weld joint 192. As indicated by dashed lines 196 in FIG. 16, the compressive residual stress region 194 may comprise a circumferential band that extends about the guidewire 180 at the region of the joint 192.

Turning now to FIGS. 17-20, a laser shock peening process for producing a tubular member having a number of internal ridges will now be described. The process, represented generally by reference number 198 in FIG. 17, may begin with the step of providing a high-energy laser apparatus 200 configured to direct an intense laser beam 202 onto the target surface 204 of a metallic mandrel 206. In the illustrative embodiment depicted in FIG. 17, the metallic mandrel 206 has a circular profile which, when used in an extrusion die, can be used to form a tubular member having a circular interior. It is contemplated, however, that the interior may have any number of desired shapes.

A sacrificial absorption overlay 208 may be applied to the target surface 204 of the mandrel 206. The absorption overlay 208 may include one or more materials that are substantially opaque to radiation, causing the absorption overlay 208 to absorb the laser beam 202 and form a number of indents 210 on the target surface 204. A confining medium may also be used to increase the magnitude of the induced pressure shock wave. In the illustrative embodiment of FIG. 17, for example, a jet of water 212 emitted from a nozzle 214 may be directed onto the target surface 204 of the mandrel 206 to form an acoustic barrier for the induced pressure shock wave.

With the laser apparatus 200 directed towards the mandrel 206, one or more laser beam 202 pulses can be directed onto the absorptive overlay 208 while rotating and periodically moving the mandrel 206 across the path of the laser beam 202. In an alternative configuration, the mandrel 206 can remain stationary while the high-energy laser apparatus 200 is rotated and periodically advanced across the surface of the mandrel 206. Using either embodiment, the indents 210 can be arranged in any pattern or array on the mandrel 206, as desired. In the illustrative embodiment depicted in FIG. 17, for example, the indents 210 are shown arranged in several circumferential bands along the length of the mandrel 206.

Figure 17:
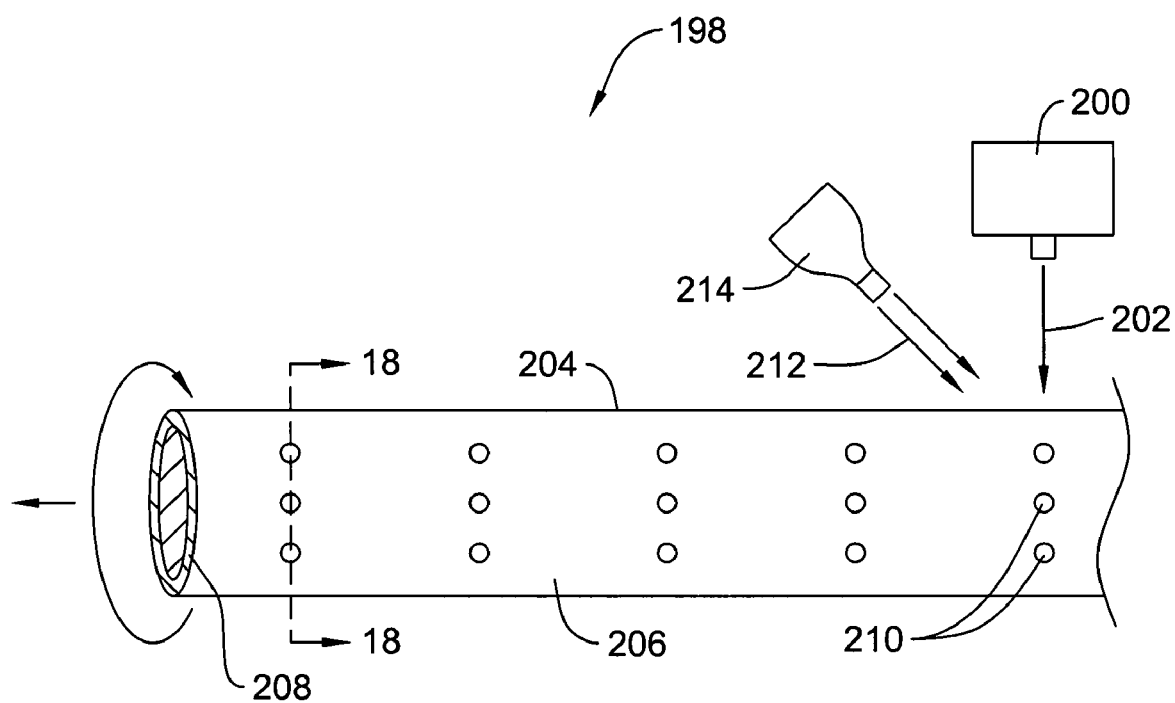
FIG. 17 is a diagrammatic view showing the formation of a number of indents on a mandrel using an illustrative laser shock peening process.
Figure 18:
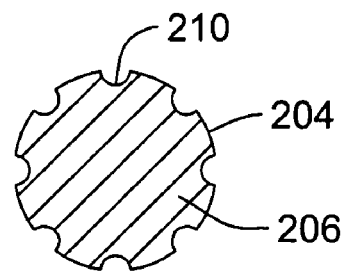
FIG. 18 is a cross-sectional view along line 18-18 of FIG. 17, showing the circumferential arrangement of the indents about the mandrel.
Figure 19:
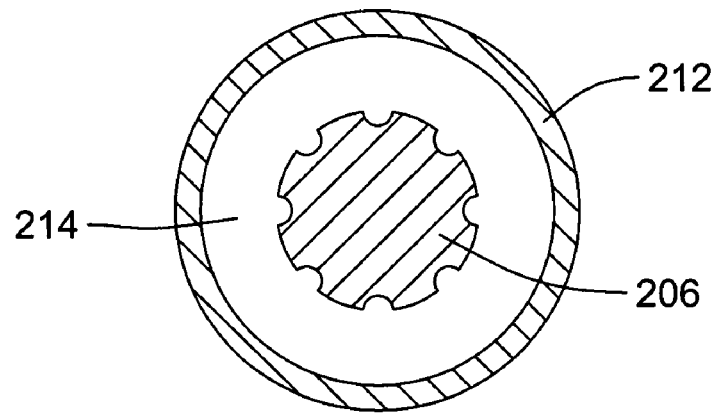
FIG. 19 is another cross-sectional view showing the indented mandrel of FIG. 17 disposed within an extrusion die.

FIG. 18 is a cross-sectional view showing the indented mandrel 206 across line 18-18 of FIG. 17. As can be seen in FIG. 18, the indents 210 are formed circumferentially about the target surface 204 of the mandrel 206. For sake of clarity, only 8 indents 210 are shown about the mandrel 206. In actual practice, however, a greater or smaller number of indents 210 can be formed about the target surface 204, as desired.

Figure 20:
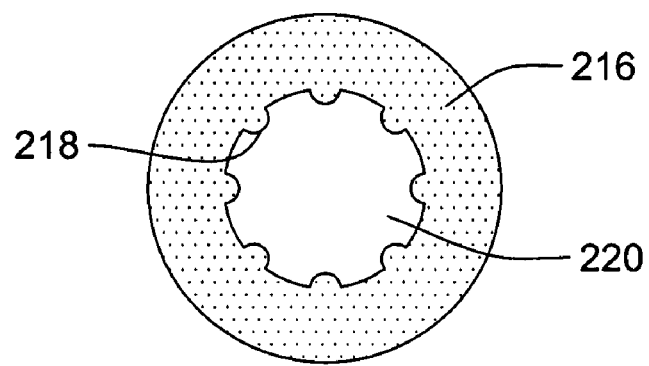
FIG. 20 is a cross-sectional view showing the profile of an illustrative tubular member extruded from the indented mandrel and die of FIG. 19.

Once the desired pattern of indents 210 has been formed on the target surface 204, a tubular member is then created by extruding a polymeric material through a die using the indented mandrel 206. As can be seen in cross-section in FIG. 19, for example, the indented mandrel 206 can be placed within a circular extrusion die 212 to form a tubular member. The annular space 214 between the extrusion die 212 and indented mandrel 206 can be injected with a polymeric material that can be used to produce a tubular member having a number of internal ridges. As can be seen in FIG. 20, for example, the extrusion die 212 and indented mandrel 206 can be used to form a tubular member 216 having a number of internal ridges 218 disposed within its interior 220 corresponding in size and shape with the indents 210 formed on the mandrel 206. In use, these internal ridges 218 reduce the amount of friction within the interior 220 of the tubular member 216 as it is advanced over a guiding member such as a guidewire or guide catheter.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A laser shock peening process for producing one or more vertical compressive residual stress regions in a medical device, the process comprising the steps of
providing a medical device having a target surface to be irradiated;
applying an absorption overlay onto the target surface of the medical device;
providing a high-energy laser apparatus adjacent to the medical device, the laser apparatus including a laser source having a beam intensity sufficient to induce a pressure shock wave within the medical device; and
directing one or more laser beams onto the absorption overlay to produce two or more simultaneous laterally overlapping shock waves which result in the formation of one or more vertical compressive residual stress regions within the medical device.

2. The laser shock peening process of claim 1, wherein said one or more compressive residual stress regions includes a pattern or array of indents.

3. The laser shock peening process of claim 1, wherein said one or more compressive residual stress regions includes a longitudinal pattern or array of indents.

4. The laser shock peening process of claim 1, wherein said one or more compressive residual stress regions includes a spiraled pattern or array of indents.

5. The laser shock peening process of claim 1, wherein said high-energy laser apparatus includes a holographic optical element.

6. The laser shock peening process of claim 1, wherein said one or more laser beams comprises a single laser beam.

7. The laser shock peening process of claim 6, wherein said absorption overlay includes a pattern that, when irradiated with pulses from the laser beam, induces multiple pressure shock waves within the medical device.

8. The laser shock peening process of claim 1, wherein said one or more laser beams comprises two adjacently pulsed laser beams.

9. The laser shock peening process of claim 1, wherein said medical device comprises a stent.

10. The laser shock peening process of claim 1, wherein said medical device comprises a guidewire.

11. The laser shock peening process of claim 1, wherein said medical device comprises a tubular member.

12. The laser shock peening process of claim 1, further comprising a confining medium.

13. A laser shock peening process for producing one or more vertical compressive residual stress regions in a medical device, the process comprising the steps of:
- providing a medical device having a target surface to be irradiated;
- applying an absorption overlay onto the target surface of the medical device;
- providing a high-energy laser apparatus adjacent to the medical device, said laser apparatus including a laser source having a beam intensity sufficient to induce a pressure shock wave within the medical device; and
- directing one or more laser beams through a confining medium and onto the absorption overlay to produce two or more simultaneous laterally overlapping shock waves which result in the formation of one or more vertical compressive residual stress regions within the medical device.

14. The laser shock peening process of claim 13, wherein said one or more vertical compressive residual stress regions includes a pattern or array of indents.

15. The laser shock peening process of claim 13, wherein said one or more vertical compressive residual stress regions includes a longitudinal pattern or array of indents.

16. The laser shock peening process of claim 13, wherein said one or more vertical compressive residual stress regions includes a spiraled pattern or array of indents.

17. The laser shock peening process of claim 13, wherein said high-energy laser apparatus includes a holographic optical element.

18. The laser shock peening process of claim 13, wherein said one or more laser beams comprises a single laser beam.

19. The laser shock peening process of claim 18, wherein said absorption overlay includes a pattern that, when irradiated with pulses from the laser beam, induces multiple pressure shock waves within the medical device.

20. The laser shock peening process of claim 13, wherein said one or more laser beams comprises two adjacently pulsed laser beams.

21. The laser shock peening process of claim 13, wherein said medical device comprises a stent.

22. The laser shock peening process of claim 13, wherein said medical device comprises a guidewire.

23. The laser shock peening process of claim 13, wherein said medical device comprises a tubular member.

\* \* \* \* \*